(12) United States Patent
Carlsson et al.

(10) Patent No.: US 6,737,278 B1
(45) Date of Patent: May 18, 2004

(54) LIGAND BINDING ASSAY AND KIT WITH A SEPARATION ZONE FOR DISTURBING ANALYTES

(75) Inventors: Jan Carlsson, Uppsala (SE); Maria Lonnberg, Knivsta (SE)

(73) Assignee: Pharmacia & Upjohn Diagnostic AB, Uppsala (SE)

( * ) Notice: Subject to any disclaimer, the term of this patent is extended or adjusted under 35 U.S.C. 154(b) by 0 days.

(21) Appl. No.: 09/673,882

(22) PCT Filed: Apr. 30, 1999

(86) PCT No.: PCT/SE99/00722

§ 371 (c)(1),
(2), (4) Date: Jan. 5, 2001

(87) PCT Pub. No.: WO99/60402

PCT Pub. Date: Nov. 25, 1999

(30) Foreign Application Priority Data

Apr. 30, 1998 (SE) ............................................... 9801563

(51) Int. Cl.[7] .............................................. G01N 33/543
(52) U.S. Cl. ........................ 436/518; 422/56; 422/57; 422/58; 422/60; 422/61; 435/7.1; 435/7.93; 435/7.94; 435/7.95; 435/287.7; 435/287.8; 435/287.9; 435/970; 436/528; 436/810; 436/825
(58) Field of Search .............................. 422/56, 57, 58, 422/60, 61; 435/7.1, 7.93, 7.94, 7.95, 287.7, 287.8, 287.9, 970; 436/518, 528, 810, 825

(56) References Cited

U.S. PATENT DOCUMENTS

| | | |
|---|---|---|
| 4,740,468 A | 4/1988 | Weng et al. |
| 4,855,240 A | 8/1989 | Rosenstein et al. |
| 4,861,711 A | 8/1989 | Friesen et al. |
| 5,120,643 A | 6/1992 | Ching et al. |
| 5,541,069 A | 7/1996 | Mortensen et al. |
| 5,766,552 A * | 6/1998 | Doshi et al. |

FOREIGN PATENT DOCUMENTS

| | | |
|---|---|---|
| EP | 0284232 | 9/1988 |
| EP | A2378391 | 7/1990 |
| EP | A1696735 | 2/1996 |
| EP | A1702233 | 3/1996 |
| GB | A2300914 | 11/1996 |
| WO | 8808534 | 11/1988 |
| WO | A1-9622532 | 7/1996 |
| WO | A1-9735205 | 9/1997 |
| WO | A1-9836278 | 8/1998 |
| WO | A1-9857172 | 12/1998 |

* cited by examiner

*Primary Examiner*—Bao-Thuy L. Nguyen
(74) *Attorney, Agent, or Firm*—Birch, Stewart, Kolasch & Birch, LLP (57) ABSTRACT

The invention relates to a method for determining an analyte by means of binding reactions, which method comprises: i) applying the sample to an application zone for sample (ASZ) on a flow matrix in which transport of components present in the sample can take place (transport flow), the flow matrix further exhibiting: a) optionally an application zone (AR*Z) for a binding reactant (Reactant*=R*) which is analytically detectable; b) a detection zone (DZ), which is located downstream of ASZ and exhibits an additional binding reactant (Capturer) firmly anchored to the matrix, and in which a complex (signal complex) containing the Capturer and the analyte and/or Reactant* is formed during the reaction, and ii) detecting the signal complex in the detection zone, the measured signal being used for determining the analyte. According to the invention, the flow matrix comprises at least one separation zone (SZ) between ASZ and DZ, which zone exhibits a structure (ligand) having binding capability for a component that is transported in the matrix and which would affect the measurable signal if the component is transported into DZ. The invention also relates to a test kit comprising the flow matrix.

24 Claims, 2 Drawing Sheets

LIGAND BINDING ASSAY AND KIT WITH A SEPARATION ZONE FOR DISTURBING ANALYTES

This application is the national phase under 35 U.S.C. §371 of PCT International Application No. PCT/SE99/00722 which has an International filing date of Apr. 30, 1999, which designated the United States of America.

TECHNICAL FIELD OF THE INVENTION

The invention relates to a method for determining an analyte in a sample and to a kit for use in the method.

Starting from the prior art, the method of the invention comprises the steps:

i. The sample is applied in a sample application zone (ASZ) on a flow matrix in which transport of components present in the sample may take place (transport flow). The flow matrix further comprises:

a) optionally an application zone (AR*Z) for a binding reactant (Reactant*=R*) which is analytically detectable, b) a detection zone (DZ) which is located downstream of ASZ and exhibits another binding reactant (Capturer) firmly anchored to the matrix and in which a complex (signal complex) containing the Capturer and the analyte and/or the Reactant* is formed in the method.

ii. The flow is allowed to effect the transport of sample components.

iii. The signal complex is detected in the detection zone and the measured signal is used for the determination of the analyte.

The invention is primarily directed to the flow matrix which may be of the same type as those previously used in, for example, immunochromatography, see below.

Suitable binding reactants are those which participate in so-called affinity reactions, especially biospecific affinity reactions, and covalent binding reactions, especially exchange reactions between free thiol and reactive disulphide and other reactions between soft electrophiles and soft nucleophiles. Common biospecific affinity reactions are immunochemical, i.e. between antibody and antigen or hapten. Other types of bioaffine reactions are hybridization between complementary nucleic acids (including oligonucleotides), reaction between lectin and carbohydrate structure, between Ig(Fc)-structure and Ig(Fc)-binding protein, such as protein A or protein G, etc. The bioaffine reactions include the reaction between a biomolecule and a synthetically prepared ligand/capturer.

For the type of method in question, one talks about non-competitive methods, for example sandwich technique, and competitive methods. Sandwich technique usually means that an analytically detectable complex is formed in which the analyte binds to two bioaffine counterparts, one of which is analytically detectable and the other is Capturer. In common competitive variants, the analyte and an analytically detectable analyte analogue will compete for a limiting amount of bioaffine counterpart. As examples of two competitive variants may be mentioned those that use: a) competition between analyte and analyte analogue, which is labelled, for a limiting amount of ligand in the form of a firmly anchored Capturer, and b) competition between analyte and analyte analogue in the form of firmly anchored Capturer for a limiting amount of soluble and analytically detectable bioaffine counterpart.

For further information on previously used methodology within the technical field of the invention it is referred to U.S. Pat. No. 4,861,711 (Behringwerke), WO 88/08534 (Unilever). U.S. Pat. Nos. 5,120,643 and 4,740,468 (Abbott), EP-A-284,232 and U.S. Pat. No. 4,855,240 (Becton Dickinson) and WO 96/22532 (Pharmacia AB).

Heteroforms

Compounds which can compete for the binding to a counterpart via one of the above mentioned binding reactions. Heteroforms may be isoforms of proteins, e.g. isoenzymes etc. Within the term heteroforms are included inter alia different forms of bioaffine complexes which "resemble" each other by meeting the above definition. Examples are immunocomplexes where the antigen is the same but the antibody is of different class/subclass. See further under the title "Analyte" below.

Determination of whether two compounds are heteroforms to each other may be made in so-called inhibition tests.

Problems to be Solved by the Invention

The components of a sample that may affect or influence the signal that is to be detected in DZ can be divided into two main groups: a) the analyte and b) components which directly or indirectly disturb the detection. Directly disturbing components are those which interfere with the signal as such, for example fluorescent components in serum in case the complex is to be detected by fluorescence. Examples of indirectly disturbing components are heteroforms with regard to Capturer and/or an added bioaffine reactant R (for example R*). Other indirectly disturbing components, for example heterophilic antibodies, may be present in the original sample and interfere with the formation of the signal complex in DZ. In certain embodiments of the invention, ligands that are released from the separation zone of the invention may act disturbingly (see Example 1).

Problems with disturbing components in samples have often meant that for analytes that are present in low concentrations, the separation of disturbing components and the detection have been performed in different systems.

An example where after ion-exchange separation, analysis has been carried out either by immunological systems or by on-line measurement of an absorbing group (460 nm), is in the measurement of carbohydrate deficient transferrins (CDT=CD-transferrin=asialo-, monosialo- and disialo-transferrin). When CDT is present at a relatively high concentration ($10^{-9}$ M), both detection alternatives have been possible, but at lower concentrations of analyte, immunological measurement is required. The ion-exchange chromatography separation is controlled from an advanced and costly equipment, which requires specially educated personnel. Also the traditional immunological tests are expensive and require well-educated personnel.

The technique for immunological on-line measurement after a chromatographic separation step has been described by Afeyan et al. (Nature 358 (1992) 603–604) and Irth et al. (Anal. Chem. 14 (1995) 355–361). Its difficulties have been summarized by Krull et al. (LC-GC 15(7) (1997) 620–629).

Transport of whole cells into DZ may interfere with the signal from the detection complex. It is previously known to use flow matrices where the cells are captured mechanically (through filtration) in a denser pre-zone (Oudheusden et al., Ann. Clin. Biochem. 28 (1991) 55–59).

EP-A-696,735 discloses a chromatographic immunoanalytical system where, in order to extend the measuring range for the analyte, a predetermined amount of analyte-binding antibody has been immobilized in the sample application zone so that a certain amount of analyte is retained therein.

EP-A-702,233 discloses a chromatographic immunoanalytical system where, in a similar manner to that described in EP-A-696,735, a dilution effect of the sample is achieved by capturing a certain amount of analyte before it reacts with labelled reactant which is then detected in the detection zone.

WO 97/35205 discloses a chromatographic membrane for immunoanalysis having (i) a zone for the detection of labelled analyte-binding reactant which has not bound to the analyte, and (ii) a zone for the detection of the complex between analyte-binding reactant and the analyte. The relative amounts of unbound analyte-binding reactant and analyte: reactant complex gives a measure of the amount of analyte in the sample.

WO 94/06012 discloses an analytical test apparatus having a negative control zone placed before the analyte detection zone. The negative control zone has the function to indicate the presence in the sample of components that affect the analyte detection so that it becomes unreliable.

OBJECTS OF THE INVENTION

A first main object of the invention is to create a simple and rapid method that facilitates the determination of an analyte in the presence of disturbing components. A particular object is to avoid problems with disturbing components that are soluble or suspendable in liquid media of interest.

A second main object of the invention is more rapid and simpler determinations of individual heteroforms or combinations thereof, especially heteroforms, that exhibit peptide, carbohydrate or lipid structures, including various types of biologically active compounds. Among lipids are included steroids and other fat-soluble substances.

A third main object of the invention is to facilitate the measurement of analytes in the concentration range $<10^{-7}$ M, particularly $<10^{-9}$ M, especially for samples containing disturbing heteroforms of the analyte.

A fourth main object of the invention is to simplify the determination of individual heteroforms or combinations thereof in samples originating from biological materials.

A fifth main object of the invention is to provide more rapid and simpler evaluations of libraries of compounds, for example chemical libraries, such as combinatorial libraries.

A subobject of the above mentioned four main objects is to improve the possibilities of making determinations in field environment (usually semi-quantitatively) as well as in advanced laboratories (with the possibility of accurate quantification).

The Invention

The above mentioned objects may be achieved with the method mentioned in the introductory part herein, if the flow matrix contains one or more separation zones (SZ) between ASZ and DZ, which should permit at least one component, capable of influencing the signal from the signal complex in DZ, to be retarded/separated. This should take place in SZ by means of the ligand interactions mentioned below, which can be reversible or irreversible. The component may be either a disturbing component or the analyte. If the component is not an analyte, the retardation means that the component (or components) migrates more slowly than the analyte through SZ or is bound irreversibly to SZ and thereby is prevented from reaching DZ such that the detection of analyte in DZ essentially will not be disturbed by the component (or components) in question. Usually, this means that there should be a sufficient amount of ligand for substantially all of the disturbing component or components in the sample to be affected. "Substantially all" depends on the relative concentrations of the component(s), but usually means that at least 90%, preferably at least about 95%, and more preferably at least 99% of the disturbing component(s) are retarded or captured in the separation zone. The component may be the analyte if it is desired to study the capability of one or more ligands to bind the analyte. In this case such a ligand is immobilized in the separation zone.

The choice of retarding structure/ligand in the separation zone is determined by the components that are retarded. The retardation may be based on various more or less specific interactions between the ligand structure and the component (s) to be retarded; see below under the title "Separation zone". After the passage of SZ, the analyte will migrate with the transport flow to the detection zone (DZ), in which a complex containing the Capturer and the analyte and/or R* are formed.

In those cases where it is intended to retard one or more disturbing components, the formation of signal complexes will take place in the absence thereof. The detection of signal complexes in DZ may be taken as a qualitative or quantitative measure of the analyte.

In those cases where it is intended to retard the analyte, the point of time for the formation of a signal complex will be changed, or, if the analyte-ligand binding in SZ is irreversible, the formation of a signal complex may be completely inhibited. The formation of a signal complex in DZ will be a measure of the capability of the analyte to bind to the ligand in SZ.

BRIEF DESCRIPTION OF THE DRAWINGS

FIGS. 1–3 illustrate different variants of flow matrices according to the invention.

A more detailed description of FIG. 1 is given under the title "Matrix and transport flow", and of FIGS. 2–3 in the introduction to Example 1. The flow matrices represented by FIGS. 1–3 may in principle have any of the geometric embodiments below.

Matrix and Transport Flow

The matrix is of the same type as those previously used in so-called immunochromatographic determination methods (flow matrix) and defines the room in which reactants and sample components are transported. The matrix may thus be the internal surface of a single flow channel (for example a capillary), the internal surface of a porous matrix having a penetrating system of flow channels (porous matrix) etc. The matrix may be in the form of monolith, sheet, column, membrane, separate flow channel(s), for example of capillary dimensions, or aggregated systems of such flow channels etc. They may also be in the form of particles packed in column cartridges or in cut grooves, compressed fibres etc. Another alternative is so-called nanocolumns for liquid chromatography, i.e. silicon or quartz plates having channels of about 2 µm or less prepared by microlithography (see e.g. He. B., et al., Anal. Chem. 1998, 70, 3790–3797). The inner surface of the matrix, i.e. the surface of the flow channels, should be sufficiently hydrophilic to permit aqueous media (primarily water) to be transported through the matrix, either by means of capillary force or by means of applied pressure or suction. The smallest inner dimension of the flow channels (for round channels measured as a diameter) should be sufficiently great to permit transport through the matrix of analyte, added reactants, and components that interfere in the detection zone and that are to be retarded in SZ. The rule of thumb is that suitable matrices may be selected among those with flow channels having a smallest inner dimension in the range of 0.1–1000 µm, with preference for 0.4–100 µm if the matrix has a system of communicating flow channels. Flow channels having their smallest dimension in the upper part of the broad range (up to 1000 µm) are primarily of interest for flows driven by externally applied pressure/suction.

Suitable matrices are often built up from a polymer, for example nitrocellulose, polyester, polyethersulphone, nylon, cellulose nitrate/acetate, cellulose, regenerated cellulose. Advantageously, these membranes may be provided with a tight backside of e.g. polyester.

The material of the matrix as well as the physical and geometric design of the flow channels may vary along the flow depending on the intended use of a certain part of the matrix [WO 96/22532 (Pharmacia AB); WO 94/15215 (Medix)]. One and the same matrix may comprise several transport flows that are parallel or directed radially from a common center, for example in the form of separate channels. In some of the most important embodiments, at least the detection zone and the most adjacent parts of the matrix should be in such a form that the transport flow into, in and out of DZ may take place laterally in the matrix, i.e. at least this part of the matrix is in the form of a membrane strip or plate having cut grooves or the like.

Various flow matrices that may be used in the type of tests in question are described in prior patent publications. See e.g. U.S. Pat. No. 4,861,711 (Behringwerke), WO 88/08534 (Unilever), U.S. Pat. Nos. 5,120,643 and 4,740,468 (Abbott), EP-A-284,232 and U.S. Pat. No. 4,855,240 (Becton Dickinson); WO 96/22532 (Pharmacia AB).

Figure 1:
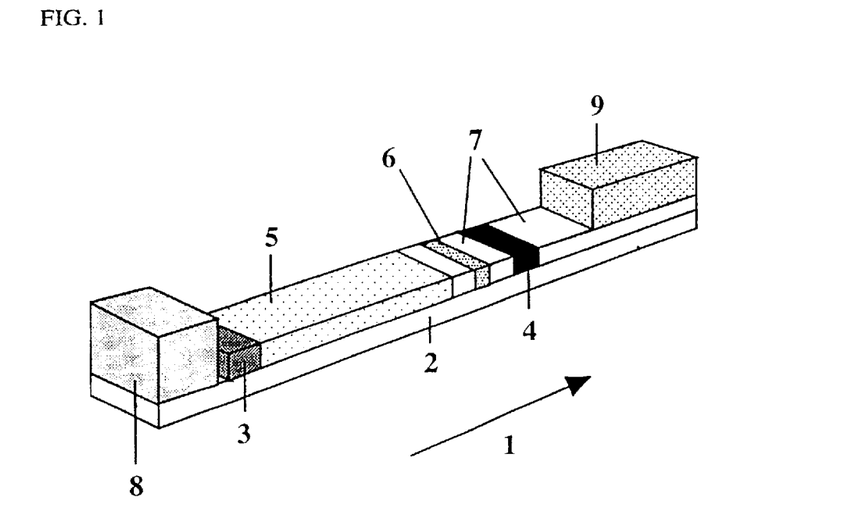
FIG. 1 is a simple variant having an ASZ, an ARZ, a SZ and a DZ. ARZ and ASZ are separated.

The most important embodiment of the invention at the priority date is based on liquid transport in a flow matrix which is in the form of e.g. a membrane strip (see FIG. 1). The strip is made up of a matrix that defines a transport flow (1) and is applied to a liquid-tight backing (2), suitably of plastic. On the matrix there is an appplication zone for sample (3, ASZ) and a detection zone (4, DZ) located downstream thereof. The transport flow is in the direction from ASZ towards DZ. Between the sample application zone (ASZ) and the detection zone there is a separation zone (5, SZ). In the transport flow there may, if required by the particular embodiment, also be application zones (6) for additional reactants (R, for example R*, with application zone ARZ, for example AR*Z). Between said zones there may be zones (7) the only function of which is to transport reactants. The position of an application zone ARZ (AR*Z) is determined by the test protocol to be used, and may be upstream or downstream of or coincide with ASZ. For the case that ARZ (for example AR*Z) is upstream of ASZ, it may be advantageous if the addition of liquid in ASZ takes place substantially simultaneously as the addition of liquid in the zone ARZ (AR*Z) located upstream thereof. See our earlier filed international patent application PCT/SE98/02463 (incorporated by reference herein). For certain types of test protocols, ARZ (AR*Z) may coincide with DZ.

In some embodiments it is advantageous if a reactant R, for example R*, is pre-deposited. This is especially the case if ARZ is located downstream of ASZ and the test protocol variant used is simultaneous, i.e. the reactant R and the analyte are to migrate into DZ substantially simultaneously.

In the cases where it is desired to use variants that are sequential in the sense that the analyte is to be transported into DZ before the reactant (R), R should be added after the sample has passed ARZ if the application zone for reactant (ARZ) is downstream of ASZ. Sequential methods may also be achieved if ARZ is upstream of ASZ, in which case R optionally may be pre-deposited in ARZ.

In alternative embodiments, reactants (R), for example R*, may migrate into DZ in separate transport flows from another direction than that of the flow that transports the analyte into DZ. See, for example, U.S. Pat. No. 4,855,240 (Becton & Dickinson).

In one and the same transport flow there may be several detection zones intended for different analytes or different concentration ranges of the same analyte. For the case that the analytes are different, the Capturers in the respective DZ must, of course, not exhibit any substantial cross-reactivity against any of the analytes.

The transport flow from ASZ through the separation zone (SZ) and further to the detection zone (DZ) may be a liquid flow driven by capillary force. When necessary, the flow matrix may exhibit a liquid reservoir (8) in the form of a porous matrix that is soaked with transport liquid and applied upstream of ASZ and/or a sucking porous matrix (9) placed downstream of DZ. The liquid reservoir and the sucking matrix assist in maintaining the flow. Liquid flow may also be achieved by means of pressure or suction through the matrix. Thus, the pressure may be driven hydrostatically, for example by a part of the matrix being designed as a minicolumn placed vertically and with its outlet in direct liquid communication with a horizontally located flow matrix. In the latter form, the horizontally located part of the matrix may be in the form of a strip/membrane. An alternative for transport of analyte, reactants and disturbing components may be the application of an electric field across the matrix.

Similar sequences of zones, like that in FIG. 1, may also be constructed for other types of flow matrices, for example capillary tubes and matrices in which the transport flow may be in depth.

One or more matrices/transport flows according to the above may be placed together, for example on a common backing, optionally with a liquid barrier between them. Optionally, the flows may have a common ASZ, a common ARZ (AR*Z) etc. As a rule, DZ is separate for each transport flow.

In the above mentioned variants, matrices having a separation zone may be used to determine one heteroform (analyte). A matrix without separation zone may be used to determine all heteroforms of the analyte that may be present in the sample in an analogous manner to that for the analyte. By combining these two types of zone sequences, relative as well as absolute quantities of analyte in the sample may easily be measured.

Separation Zone (SZ)

The separation zone exhibits a ligand/structure having binding capability for one or more sample components that would have disturbed the detection in DZ. A characteristic feature is that the separation is achieved by means of some type of specific/selective binding reaction and not because the matrix in SZ provides a mechanical obstacle for disturbing components (filtration). Guiding principles for the choice of separating/retarding ligand/structure, especially with regard to specificity, binding strength (affinity), and kinetics are the same as in affinity chromatography, including ion-exchange chromatography, covalent chromatography, and biospecific analytical methods in which solid-phase technology is used for capture. With regard to binding strength (affinity, avidity) and kinetics, the main object of the presently preferred variants of the invention is to retard disturbing components in relation to the analyte so that detection in DZ may take place without presence of these components. Generally, this means that the disturbing components should be retarded as effectively as possible or be bound as strongly and quickly as possible in the separation zone.

The ligands that make separation in SZ possible may thus be a) charged (anionic, cationic, amphoteric=ion-exchange ligands), amphoteric/amphiphilic, bioaffine, chelating, sulphur-containing (primarily thioether for so-called thiophilic affinity), those permitting covalent chromatography (reactive disulphide such as pyridyl disulphide) or $\pi$-$\pi$ interaction, hydrophobic etc.

In those cases where disturbing components are to be retarded, the rule of thumb is that the binding capability of the ligand to one or more disturbing components should be stronger than that to the analyte. This applies to the conditions used for the separation in SZ. Factors that determine how the separation will succeed are the length of the separation zone, ligand density, ligand availability, temperature, flow velocity, buffer, ion-strength, pH, etc.

Among biospecific affinity ligands, primarily so-called immunoligands are noted, i.e. antibodies and antigen-binding fragments thereof, and antigen and hapten. Other examples of affinity ligands are lectin (for example, sialic acid-binding lectins); Ig(Fc)-binding protein (such as Protein A and G); nucleic acid, such as oligo- or polynucleotide in single or double-stranded form, analogues of substrates for enzymes, enzyme inhibitors, etc. For biospecific affinity ligands, the specificity may be directed towards one or more binding sites on the component(s) to be retarded. The corresponding binding sites should not be available to the same degree on the analyte (by which is also intended the case that they do not even exist in non-exposed form).

The ligands/structures in question may be anchored to the separation zone, either by covalent binding to the matrix, via physical or biospecific adsorption. Examples of the latter is the interaction between biotin and streptavidin, between highly affine antibody and hapten etc. The anchorage to the matrix may take place via a polymer or other substituent which in turn carries covalently, physically adsorptively, or biospecifically bound ligands that are used in the separation. Another possibility is deposition of polymeric particles which exhibit a desired type of ligand. The particles may be of hydrophilic or hydrophobic character and to which a compound exhibiting the ligand structure has been adsorbed or covalently bound. The technique for binding a separating ligand to the matrix SZ may basically be selected in the same way as previously known for the Capturer in DZ. See, for example, our earlier filed international patent applications PCT/SE98/02462, PCT/SE98/02463 and PCT/SE98/02464 which are hereby incorporated by reference with regard to the introduction of Capturer into the detection zone. In this connection it may be mentioned that there are commercially available membranes which have covalently bound ligands, for example DEAE cellulose paper (diethyl aminoethyl) (DE81, Whatman International Ltd, England).

Detection Zone

The Capturer in the detection zone may be selected according to the same rules as those applying to the ligand in the separation zone, with the proviso that the binding capability of the Capturer should be directed towards the analyte and/or towards an analyte-related reactant. It is advantageous to choose highly affine Capturers with rapid kinetics for capture of the ligand. It is primarily of interest to use antibodies or antigen/hapten for which it is often easy to find highly affine antibodies.

By analyte-related reactant is intended a reactant (R) that is added and when migrating through DZ may bind to the Capturer in an amount that is related to the presence of analyte in the sample. Examples of analyte-related reactants are R* in the form of a) labelled analyte analogue in competitive methods that use competition for a limiting amount of solid-phase-bound anti-analyte antibody, and b) labelled or non-labelled soluble anti-analyte antibody in methods that use competition/inhibition between solid-phase-bound analyte analogue and analyte for a limiting amount of anti-analyte antibody in dissolved form.

The Capturer may be anchored to the detection zone by a technique analogous to that used to bind the ligand to the separation zone.

It may be suitable to combine a separation principle in the separation zone with a different capturing principle in the detection zone, e.g. ion-exchange chromatography for separation and immunochemical adsorption for capture in DZ. In some situations it may be practical to use the same principle for retardation and capture in the two zones (e.g. two monoclonal antibodies having different specificities, see the Examples).

Analyte

By analyte is intended the compound or compounds that are determined quantitatively or qualitatively. Quantitative determination relates to the measurement of quantities in absolute as well as relative terms. Qualitative determination of an analyte refers to detecting the existence or non-existence of something (yes/no test) or qualitative properties of a compound, such as capability of affinity-binding to a certain ligand.

By relative measurement is intended that the measurement value obtained is a ratio of the sum of one or more selected heteroforms and the sum of another combination of heteroforms. An example is the ratio of analyte amount and total amount of all heteroforms with regard to a certain counterpart (total amount includes the amount of analyte).

The invention is applicable to analytes that may function as a binding reactant. This means that the analyte basically can be any substance for which it is possible to provide a Capturer as above. As specific examples may be mentioned antigen/hapten, enzyme or antibody or nucleic acid which completely or partly are in single-stranded form. The analyte may exhibit amino acid/peptide, carbohydrate or lipid structure.

Particularly great advantages are obtained for analytes existing together with heteroforms with regard to binding capability to Capturer and/or an added reactant R, for example R*. This applies particularly to the cases where the analyte is in sample concentrations which are $<10^{-7}$ M, especially $<10^{-9}$ M. As examples of this type of heteroforms may be mentioned: a) Compounds which differ from each other in charge, such as isotransferrins with, for example, CDT as analyte, isohemoglobins with, for example, HbAlc as analyte; b) Compounds which differ from each other in certain parts of the basic structure, such as additionally inserted or cleaved (e.g. by degradation) amino acids, or partial differences in peptide chains; c) Compounds which differ from each other due to the fact that different substances/structures have been added to a basic structure, for example covalently bonded carbohydrate structures; d) macromolecules consisting of two or more subunits which in the macromolecule bind to each other via non-covalent bonds, such as bioaffine bonds between receptor and ligand in receptor-ligand complexes and between antigen and antibody in immunocomplexes, or via cystine bridges, for example between the chains of an antibody.

Examples of potential uses/analytes are:

a) The analyte is a heteroform which differs from other heteroforms with regard to carbohydrate contents (glycosylation), for example glycoproteins having the same or a similar protein part. Variations in this type of heteroforms are known in a number of disease conditions such as cancer, inflammation and liver diseases. (Turner G A, "N-glycosylation of serum proteins in disease and its investigation using lectins", Clin. Chim. Acta 208 (1992) 149–171; and Varki A, "Biological roles of oligosaccharides: all of the theories correct", Glycobiology 3(2) (1993) 97–130). Particularly may be mentioned the measurement of i) combinations of asialo-, monosialo- and disialo-transferrin for which separation may be performed by ion-exchange ligand and also by lectin ligand in SZ, and ii) HbAlc which may be separated by means of ion-exchange or boronate ligand. Variations in the carbohydrate contents of proteins are also known in normal biological changes, for example during the menstrual cycle and for differences in age and sex.

b) The degree of glycosylation of recombinant proteins could be determined by means of ion-exchange, lectin or boronate ligands in SZ. The analyte will in this case be the fraction of a recombinant protein that does not contain a carbohydrate structure that binds to the ligand in SZ and therefore migrates most rapidly through SZ.

c) Recombinant proteins into which a separation handle has been inserted, for example a histidine sequence or an IgG-binding sequence, and where total cleavage of the handle is important, could be checked after separation in SZ by means of a metal chelate ligand or and IgG(Fc)-ligand, respectively. The analyte will in this case be the fraction of the recombinant protein from which the histidine sequence or the Ig(Fc)-binding sequence, respectively has been cleaved off.

d) Enzymes could be separated into an active and an inactive form by means of a ligand in SZ which is a substrate analogue or an inhibitor of the enzyme in question. The analyte will be the inactive enzyme.

e) Proteins, peptides or other biomolecules which exert their biological function by binding to a specific receptor could be separated by means of a ligand in SZ which is a receptor for the biomolecule. The analyte will be the fraction of the molecules that lack or have a reduced capability of binding to the receptor.

f) Proteins (e.g. IgE) may in vivo have autoantibodies (IgG, IgA, IgM) bound thereto. These autoantibodies give rise to, on the one hand, a differing response in immunochemical determination of the protein, and, on the other hand, an altered turnover rate/function. By using antibodies to the autoantibodies in question as ligand in the separation zone, autoantibodies in free and immunocomplex-bound form may be separated and the amount of the free form of the protein (=analyte, e.g. of IgE) may be calculated.

g) By means of a monoclonal antibody directed against a certain binding site of a protein and immobilized to SZ, the presence of heteroforms to the protein which do not exhibit the binding site (=analyte) could detected by quantification in DZ.

h) The presence of different substances bound to transport proteins, e.g. a drug bound to albumin, could be measured by using suitable ligands in SZ. By the choice of a suitable ligand in SZ, transport proteins with or without bound drug may be measured in DZ.

i) IgG and IgA in serum may in certain rheumatic or autoimmune diseases have an increased adsorption to different surfaces. By anchoring ligands in the separation zone which are capable of binding to IgG and IgA with changed properties, it will be possible to measure the proportion of IgG and IgA with unchanged adsorption properties (=analyte) in DZ. By having the corresponding autoantigen/hapten as Capturer in DZ, specific autoantibodies of IgG or IgA class could be measured with better sensitivity.

j) Many biologically active compounds (for example, peptides or steroids) are transported in serum in the form of complexes with binder proteins. By using antibodies against the binder protein as ligand in SZ, the non-complex-bound (free) form of these compounds (=analyte) could be determined immunochemically in the following detection zone. Examples are triiodothyronine and thyroxine which are transported bound to thyroxine-binding globulin (TBG) or thyroxine-binding prealbumin (TBPA). Analogously, free forms of estradiol and testosterone which are transported in bound form with sexual hormone-binding globulin may be measured.

k) The binding capability of a first compound (=analyte) for a second compound may be determined with the invention. In this embodiment, one may have the second compound as ligand in SZ, and a Capturer with a known binding capability to the analyte in DZ. Capture/retardation in SZ will be a measure of the binding capability of the analyte and may be measured in DZ.

This embodiment of the invention may be particularly advantageous in the screening of different libraries of compounds with the library members as ligands in SZ (chemical libraries, for example).

l) Degradation isoforms of proteins where amino acids have been cleaved off, can be determined by the invention. For example, degradation isoforms of creatine kinase (CK) are interesting cardiac markers.

Detection in DZ and Labelled Reactant (R*)

Detection and quantification of signal complexes may be performed by means of an analytically detectable reactant (Reactant*=R*). For those cases where the analyte per se is detectable and is part of a signal complex, detection and quantification may take place without using R*.

R* is usually a biospecific affinity reactant which is labelled with an analytically detectable group, such as an enzymatically active group, radioactive group, fluorescent group, chomogenic group, hapten, biotin, particles, etc. Analytically detectable reactants (R*) also include reactants which per se have binding sites or properties which may be detected analytically when the reactant is part of the signal complex. Examples of such binding sites are Ig-class- and Ig-subclass-specific determinants when the reactant is an antibody and the antigen-binding part thereof is used to form the complex in the detection zone.

Usual forms of analytically labelled reactant are labelled antibody and labelled antigen/hapten. Labelled antibody has its primary use in A) non-competitive techniques, such as sandwich technique, in which the capturer is
   a) an antibody which is directed against the same antigen (=analyte) as the labelled antibody, or
   b) an antigen/hapten, or
B) competitive techniques in which competition takes place between an analyte and a solid phase-bound analyte analogue for a limiting amount of anti-analyte antibody and the detection of free or occupied sites on the solid phase may be performed by means of labelled anti-analyte antibody and anti-anti-analyte antibody, respectively.

Labelled antigen/hapten has its Primary use in

A) competitive techniques in which a labelled antigen/hapten is allowed to compete with an unlabelled antigen/hapten for a limiting amount of antibody (Capturer), or
B) sandwich-techniques in which antigen/hapten-specific antibody is determined with anti-antibody as Capturer.

Examples of variants of the invention in which an analytically detectable reactant (R*) is not utilized are those where the analyte per se is detectable when it is part of the complex in DZ. This is illustrated with enzyme as analyte in combination with a substrate that gives an analytically detectable product, for example a substrate that gives a coloured or fluorescent product that should be insoluble.

R* may, but need not, exhibit binding capability to the disturbing components that are separated in SZ. To the extent that R* has binding capability, the application zone thereof should be located downstream of the separation zone (SZ), unless it is desired to measure the level of disturbing heteroforms by means of the amount of R* binding to SZ.

A particularly useful labelling group is particles which optionally contain one of the above mentioned detectable groups, such as fluorophoric group or chromogenic group (fluorescent and coloured particles, respectively). Useful particles often have a size in the range of 0.001 to 5 $\mu$m, with preference for the range of 0.05 to 5 $\mu$m. The particles may be of colloidal dimensions, so-called sol (i.e. usually spherical and monodisperse having a size in the range of 0.001 to 1 $\mu$m). Especially may be mentioned metal particles (for example, gold sol), non-metal particles (for example, $SiO_2$, carbon, latex and killed erythrocytes and bacteria). Also particles of non-colloidal dimensions have been used. These particles have been more or less irregular and more or less polydisperse (for example, carbon particles <1 $\mu$m; Pharmacia AB, WO 96/22532).

When particles are the label group in the invention, the complex in DZ may often be detected visually or by optical measuring equipment (e.g. a CCD camera coupled to a computer with special software for image analysis or a laser scanner).

For particles as the label group, it is referred to WO 88/08534 (Unilever); U.S. Pat. No. 5,120,643 (Abbott); EP-A-284,232 (Becton Dickinson) and others.

Samples

The invention is primarily intended for biological samples, for example, blood (serum, plasma, whole blood), saliva, tear fluid, urine, cerebrospinal fluid, sweat, etc. The invention is also applicable to other samples, such as fermentation solutions, reaction mixtures, solutions containing a certain protein for which the binding capability to a ligand in SZ is to be investigated, etc. See above under the title "Analytes". It may be particularly interesting to use the invention for analysis of environmental samples.

In addition to the method, the invention also relates to an apparatus and a kit, respectively, containing the above defined flow matrix.

The inventions disclosed in the above-mentioned international applications PCT/SE98/02462, PCT/SE98/02463 and PCT/SE98/02464 may in relevant parts constitute preferred embodiments of the present invention. All three applications have been incorporated by reference.

PATENT EXAMPLES

Example 1

Figure 2A:
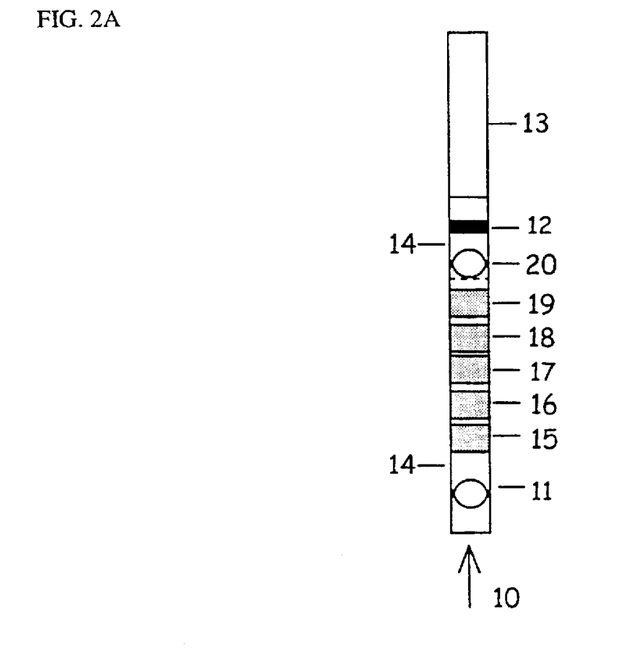
FIG. 2A differs from the variant in FIG. 1 primarily by having five separation zones with the same ligand. ARZ and ASZ are separated.
Figure 2B:
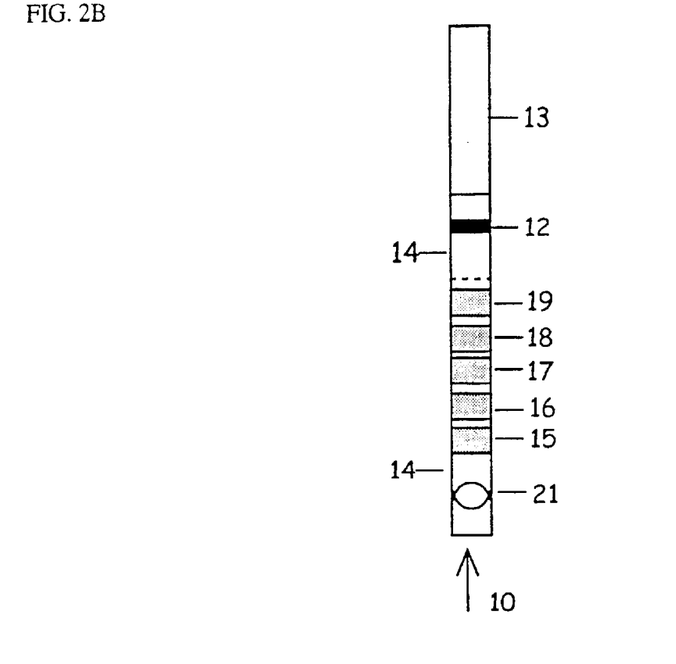
FIG. 2B is the same as the variant in FIG. 2A except that ARZ and ASZ coincide.
Figure 3:
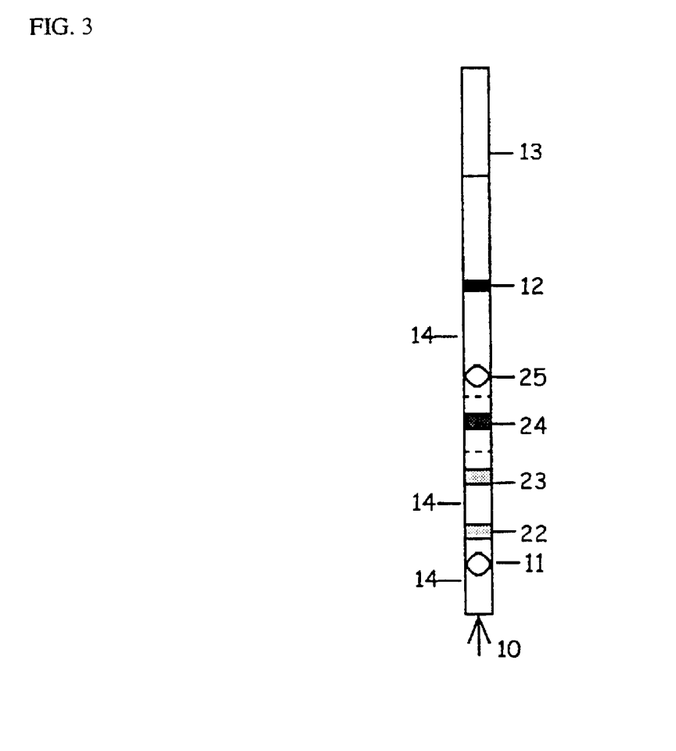
FIG. 3 illustrates the variant of flow matrix of the invention that is used in Example 1 with three separation zones, two zones (SZ1) thereof exhibiting a certain ligand and one zone (SZ2) exhibiting another ligand. ASZ and ARZ (=AR*Z) are separated.

Test Strip for Measurement of the Proportion of Free IgE, IgE Bound to IgG and Antibodies to IgE In FIGS. 2A, 2B and 3 the direction of the transport flow is indicated by an arrow (10). In each variant there may at the beginning of the transport flow be a zone ASZ (11) for sample, downstream thereof a zone DZ (12), at the end of the transport flow a sucking part (13), and between each type of zone, parts which only serve as transport zones (14).

FIG. 2A

The variant according to this figure has five separation zones (SZ) in which the ligand may be the same or different or be present in different amounts (15–19) and an AR*Z (20) for reagents.

FIG. 2B

This is the same sequence of zones as in FIG. 2A except that ASZ (11) and AR*Z (20) coincide (21). This zone sequence may also be used for the cases where the analyte per se is detectable when it is part of a signal complex in DZ. An AR*Z is then not necessary.

FIG. 3

The sequence of zones according to this figure exhibits two types of separation zones SZ1 (22, 23) and SZ2 (24), respectively, and separately AR*Z (25) downstream of SZ1 (23) and SZ2 (24).

BACKGROUND

Free IgE and IgE complex-bound to autoantibody (IgA, IgG and IgM) may be of interest to measure. Above all, however, free IgE should be quantified correctly. In the current tests for measurement of IgE, the autoantibodies may bind to the same epitopes on IgE as the reagent antibodies (anti-IgE antibody) and this may then give rise to falsely too low total IgE levels that vary depending on the design of the test. By separating IgG, IgM and IgA before the measurement of IgE, free IgE may be detected. The amount of autoantibodies should also be quantified both as complexes and as free IgG antibodies directed against IgE.

The most common tests measure free antibodies by methods which use IgE bound to a solid phase (corresponding to DZ) with which a heavily diluted serum sample is allowed to interact. If the serum sample contains anti-IgE antibody, the latter is bound to the solid phase forming an immunocomplex. After unbound serum components have been washed away, anti-IgG antibody that is labelled (R*), e.g. with enzyme, is added. Excess of labelled antibody (R*) is removed and the amount of enzyme-labelled anti-IgG antibody (R*) bound to the immobilized immunocomplex is determined by the addition of a suitable substrate. The sensitivity of these tests is limited by the unspecific binding of IgG to the solid phase. The IgE-specific part of the IgG population is generally very small and may be difficult to distinguish from the amount of unspecifically bound IgG. By capturing IgG to the solid phase and measuring the binding of IgE, this limitation may be avoided.

When measuring IgG-complex bound IgE, IgG is captured to a solid phase s (corresponding to DZ) which supports covalently bound anti-IgG antibody (Capturer). By adding labelled anti-IgE antibody (R*), the amount of complex-bound IgE may be measured.

The use of an immunoassay technique based on lateral liquid transport in membranes as described above where the flow first passes through one or more separation zones (SZ) and then a detection zone (DZ), opens many possibilities for simple measurement of IgE-IgG related parameters. If e.g. a sample that contains a mixture of free IgE and IgE bound to a human anti-IgE antibody of IgG class first is made to pass through a zone containing solid phase-bound anti-human IgG antibody (Ligand in SZ) and then a zone containing solid phase-bound anti-IgE antibody (Capturer in DZ), the sample content of complex between IgE and anti-IgE antibody of IgG class will be bound in the separation zone while free IgE passes to the detection zone where it is determined by adding labelled anti-IgE antibody (R*) upstream of the detection zone (12) but downstream of the separation zones (15–19) for passage only through the detection zone (addition in zone 20 in FIG. 2A). By having anti-IgE antibody (R*) pass also the separation zone, the amount of IgE-IgG complex captured in the separation zone by binding to anti-human IgG (Ligand) may also be determined (ASZ and AR*Z coincide) (addition in zone 21 in FIG. 2B, ASZ common with AR*Z). In the separation zone there are, in addition to complex between IgE and anti-IgE antibody of IgG class, also free antibodies against IgE. The amount of the latter may be determined by having labelled IgE (R*$_1$) pass through the separation zone. Labelled IgE (R*$_1$) is then added in a separate test to the membrane strip upstream of SZ. See FIG. 2B.

When the amount of IgG is very high in serum, several bands with high concentrations of anti-IgG must be used as SZ. Both complex-bound and free anti-IgE antibodies will then be distributed over several bands due to the total amount of IgG, and the sum of the signal intensities of these bands gives the amount of antibodies against IgE.

In the example below, the test principle of artificially prepared complexes of IgE and IgG is demonstrated. The complexes have been prepared with monoclonal antibodies against IgE, and antibodies against mouse-IgG have therefore been bound to the separation membrane. In the detection system, antibodies to IgE directed against other epitopes than the complex-forming antibody have been used. This makes it possible to measure the complex equally well as free IgE in the detection system.

Separation Membrane 1 (SZ1)

Sheep anti-mouse IgG(Fc) (Ligand 1) was coupled to polystyrene aldehyde particles (0.29 μm diameter, IDC, Portland. Oreg., U.S.A.) by mixing 1.0 mg/ml of antibodies and 20 mg/ml of polystyrene aldehyde particles in 25 mM phosphate buffer, pH 6.6, at +4° C. for 20 hours. The particles were washed in 20 mM borate buffer, pH 8.6, and were reacted with 15 mg of NaCNBH$_3$ (Sigma-Aldrich Chemie, Steinheim, Germany) per 50 mg of particles for 20 hours. The particles were then washed in 20 mM borate buffer, pH 8.6, by repeated suspension, centrifugation and decanting. The particle suspension was diluted in 3% trehalose, 20 mM borate buffer, to 25 mg of particles/ml. The diluted suspension was sprayed on strips (20 cm×3 cm) of membranes of nitrocellulose (nitrocellulose on polyester, 5 μm pore size, Whatman International Ltd, England) in two 0.3 cm wide lines which were parallel to the long sides of the strips. The spraying equipment (IVEK linear striper, IVEK Corporation, Vermont, U.S.A.) delivered about 50 μg of polystyrene particles/cm for each line. The membranes were dried at room temperature and then cut to smaller pieces (0.5 cm×3 cm).

Separation Membrane 2 (SZ2)

Mouse IgG (Ligand 2) was diluted in 20 mM borate buffer to 3.4 mg of protein/ml. The diluted antibody was sprayed on strips (20 cm×4 cm) of membranes of nitrocellulose (the same type as above) in a 0.3 cm wide line (spraying equipment as above) with about 6.8 μg of antibodies/cm. The membranes were dried at room temperature and then cut to smaller pieces (0.5 cm×1 cm).

Detection Membrane (DZ)

Mouse anti-IgE monoclonal antibody (directed against domain 4 on IgE. Capturer) was diluted in 20 mM borate buffer to 1.0 mg of protein/ml. The diluted antibody was sprayed on strips (20 cm×4 cm) of membranes of nitrocellulose (the same type as above) in a 0.15 wide line (spraying equipment as above) with about 1 μg of antibodies/cm. The membranes were dried at room temperature and then cut to smaller pieces (0.5 cm×4 cm) so that the line with antibody was parallel with a short side.

Combination Membrane

See FIG. 3. A piece of separation membrane 1 (0.5 cm×3 cm, SZ1, 22 and 23, respectively, in FIG. 3) were mounted to a piece of separation membrane 2 (0.5 cm×1 cm. SZ2, 24 in FIG. 3) and the thus obtained combined separation membrane was in turn joined to a strip of the detection membrane (0.5 cm×4 cm, the line=DZ=12 in FIG. 3) (short side to short side with a gap between them). The pieces were kept together on the bottom side by adhesive tape. On the top side were placed pieces of nitrocellulose (0.5 cm×0.3 cm) (A100, 12 μm, Schleicher and Schull, Dassel, Germany) which somewhat overlapped two adjacent short sides. The latter pieces were kept in place by more adhesive tape. A cellulose filter (13 in FIG. 3) (0.5 cm×2 cm; GB 004, Schleicher and Schull, Dassel, Germany) overlapping the free short side of the detection membrane was mounted as a sucking membrane. The sequence of zones was ASZ, SZ1, SZ2, DZ.

Preparation of Carbon Particle Conjugate (R*)

Carbon Suspension (Stock Solution)

2 g of carbon particles (sp 100, Degussa, Germany) were suspended in 200 ml of 5 mM borate buffer, pH 8.4, and sonicated (VibraCell 600 W, 1.5 cm probe, Soniced Materials, Danebury, Conn., U.S.A.) in an ice-bath for 3×5 minutes at 100% amplitude and with 9.9+2 seconds pulse.

Carbon Particle Conjugate (R*)

35 μg/ml of Fab'2 of anti-IgE monoclonal antibody (directed against domain 3 in IgE) and a suspension of carbon particles (250 μg /ml) were mixed for 3 hours. Bovine serum albumin (BSA) was added to 1% and the particles were mixed for another 30 minutes and then washed by means of centrifugation in 1% BSA (0.1 M borate buffer, pH 8.5, 0.05% NaN$_3$) and diluted to 0.8 mg carbon/ml in the wash buffer. The ready carbon particle conjugate was stored at +4° C. in the wash buffer.

Sample Material

Preparation of Complex Between IgE and IgG 1 mg of IgE (ND)/ml and 5 mg/ml of mouse anti-IgE monoclonal antibody (of IgG class and directed against domain 2) were reacted in 50 mM phosphate buffer, pH 7.5, for 2.75 hours at room temperature. The sample mixture (0.35 ml) was separated on Superdex™ 200 prep grade, 16/60 (Amersham Pharmacia Biotech AB, Sweden). The separation gave two discernible complex peaks, one peak corresponded to IgE-IgG and one peak corresponded to IgG-IgE-IgG.

Control with $^{125}$I-labelled Proteins (Labelled Anti-IgE Antibody and Labelled IgE)
Separation Membrane 1 (Ligand=anti-mouse IgG)

Mouse anti IgE antibody (against domain 2 of IgE) and IgE were labelled with $^{125}$I (Chloramine T) to a labelling degree of 0.03 for anti-IgE antibody and 1.5 for IgE. The labelled proteins were diluted in 6% BSA (50 mM phosphate buffer, pH 7.5): anti-IgE antibody to about 2.4 μg/ml and IgE to 0.06 μg/ml. $^{125}$I anti-IgE antibody (domain 2) was mixed with unlabelled anti-IgE antibody (against domain 2) for measuring higher levels of anti-IgE antibody. A sucking membrane (0.5 cm×2 cm, GB004, Schleicher and Schuell, Dassel, Germany) was attached with tape to one end of a piece of separation membrane 1 (0.5 cm×4 cm) with adsorbed sheep anti-mouse IgG(Fc). 10 μl of 0.1 M borate buffer, pH 8.5 (6% BSA, 0.05% NaN$_3$), followed by 10 μl of a solution of $^{125}$I-protein were applied to the free end of the separation membrane. The lateral flow was then initiated by the addition of 4×10 μl of 0.1 M borate buffer, pH 8.5 (1% BSA, 0.05% NaN$_3$) to the free end. After all liquid had migrated into the membrane, it was cut to pieces for measurement of the radioactivity in the different zones of the sheet (separation and transport zones). The measurement was made in a gamma counter, and the proportion of $^{125}$I-protein (labelled anti-IgE antibody and labelled IgE, respectively) that had been captured in the different zones was calculated after correction for the amount of free radioactive iodine. IgE did not bind any more to the separation zones in which anti-IgG antibody was the ligand than to the intermediate transport zones. More than 85% IgE passed through the membrane. On the other hand, all labelled anti-IgE antibody was bound to the two separation zones when up to 120 ng of anti-IgE antibody were added. When 1000 ng of anti-IgE antibody were added, 200 ng were bound in each anti-mouse IgG zone (separation zone) and 500 ng passed. For IgG in human serum this capacity may be sufficient if the serum is diluted 1/100 (about 1000 ng of IgG) and more anti-IgG antibody (against human IgG) is used as firmly anchored ligand.

Separation Membrane 2 (Ligand=mouse IgG)

This membrane was introduced to bind any anti-mouse IgG antibody that may have been released from the separation membrane 1 and which otherwise would be bound to the detection zone resulting in an increased background signal (anti-mouse IgG antibody has two Fab parts and may therefore simultaneously bind to R* and Capturer which both are mouse-IgG). The amount of sheep anti-IgG that was released could advantageously be bound with a separation zone containing mouse IgG before the detection zone. By means of this capturing zone (SZ2) the non-specific binding in the detection zone could be reduced by more than 6 times.

Standard Protocol for Combined Separation and Immunochemical Determination

20 μl of wash buffer (1% BSA, 0.9% NaCl, 1% Tween 20, 0.1 M borate buffer, pH 8.4, 0.05% NaN$_3$) were applied to the edge of the free end (ASZ=11 in FIG. 3) of the separation membrane 1 on a combination strip according to the above (Sequence SZ1, SZ2, DZ). Then 10 μl of IgE standard (IgE, 4–500 kU/1, 0.01-1.2 μg/ml) and sample (IgE-IgG complex with about 1 μg complex/ml and IgG-IgE-IgG complex with about 1.3 μg complex/ml), respectively, were added. Both sample and standard were diluted in 50 mM phosphate buffer, pH 7.5, containing 6% BSA and 0.05% NaN$_3$. A lateral flow was initiated by placing a 0.6 cm×0.6 cm×0.3 cm cellulose sponge containing wash buffer, 0.1 M borate buffer, pH 8.4 (1% BSA, 0.9% NaCl, 1% Tween 20, 0.05% NaN$_3$) on the free end of the separation part of the strip. The test solution migrated through the separation zones (22, 23, 24 in FIG. 3) and the detection zone (12 in FIG. 3) and into the sucking cellulose sponge (13 in FIG. 3). After 7 minutes flow, 10 μl of conjugate (R*) of carbon particles and anti-IgE antibody (0.8 mg carbon/ml in 0.1 M borate buffer, pH 8.4 (1% BSA, 0.05% NaN$_3$) were added in the position between the detection zone and the separation part (25) of the strip. After another 5 minutes flow, the detection zone was coloured grey to black. The blackening was read in a laser scanner (Ultroscan, Anersham Pharmacia Biotech AB, Uppsala, Sweden), the peak intensity was calculated and the concentration determined by reading against the IgE standard curve. The higher the IgE concentration, the blacker the signal.

As a comparison, strips having the separation zone 1 replaced by nitrocellulose without ligand (both standard and sample) were evaluated in the same way.

Results

The standards (IgE) gave the same intensity on the blackening curve in both measuring systems. The complexes (IgE-IgG and IgG-IgE-IgG) were detected by a strong black signal in DZ if SZ1 was replaced by nitrocellulose without ligand. If SZ 1 contained anti-mouse IgG as ligand, no signal could be detected in DZ for the complexes.

TABLE 1

| Sample | Separation zone (SZ1) | |
| --- | --- | --- |
| Immune complex | Without ligand | Ligand = anti-mouse IgG |
| IgE-IgG complex | 131 kU/l | <4 kU/l |
| IgG-IgE-IgG complex | 141 kU/l | <4 kU/l |

The separation zone with anti-mouse IgG thus captured up to more than 97% of the complexes.

Example 2

Determination Method for CD-Transferrin in Patient Samples
Separation Membrane Having Anion-exchanging Properties A sheet of nitrocellulose membrane (5 μm, nitrocellulose on polyester, Whatman International Ltd, England) was placed in a solution of 0.1% polyethylene imine (PEI, Sigma, St Louis, Mo., U.S.A.) in ultrapure water (Milli Q, Millipore Corp., Bedford, Mass., U.S.A.). The solution was shaken for 3 hours and then placed in 0.1% in Tween 20 for 30 minutes, air-dried and then stored in a plastic bag at +4° C. The modification degree of the membrane was checked with bromophenol blue (pK=4.1).

The function of modified membranes to interact with charged proteins was confirmed by transporting $^{125}$I-labelled proteins (bovine serum albumin, tetrasialo- and asialo-transferrin which had been labelled by the Chloramine T method) in a lateral liquid flow in strips of the sheet. The protein having the highest pI had the strongest tendency to migrate with the liquid flow. If the liquid in different tests contained an increasing concentration of NaCl (0–1000 mM), the migration rate was affected most for the proteins having the lowest pI. Both these function controls support the fact that positively charged groups had been introduced in the treatment with polyethylene imine, and that these groups can function as ion-exchanging groups towards protein and NaCl.

Detection Membrane

Anti-transferrin monoclonal antibody was coupled to polystyrene-aldehyde particles (0.29 μm diameter, IDC, Portland, Oreg., U.S.A.) by mixing 1.3 mg/ml antibody and 22 mg/ml polystyrene-aldehyde particles in 25 mM phosphate buffer, pH 6.6, at +4° C. for 18 hours. The particles were washed in 20 mM borate buffer, pH 8.4, and were reacted with 5 mg of NaCNBH$_3$ (Sigma-Aldrich Chemie GmbH, Steinheim, Germany) per 40 mg of particles per ml for 18 hours. The particles were washed in 20 mM borate buffer, pH 8.6, and diluted in 20 mM borate buffer containing 6% trehalose to 14 mg particles/ml. The diluted suspension was sprayed on strips (20 cm×4 cm) of membranes of nitrocellulose (5 µm, nitrocellulose on polyester backing, Whatman International Ltd. England) in a 1.4 mm wide line in the middle of the strip and in parallel with the long side of the strip. The spraying equipment was the same as in Example 1 and now delivered 14 µg of polystyrene particles/cm. The membranes were dried at room temperature and stored in a plastic bag at +4° C.

Combination Membrane

See FIG. 1. The end of a strip of the separation membrane (0.5 cm×3 cm) (=SZ=5 in FIG. 1) was mounted by means of tape on the underside to the end of a strip of the detection membrane that had been shortened by 0.5 cm (0.5 cm×3.5 cm, the line with antibody=DZ=4 in FIG. 1). The gap between the ends was bridged with an overlap by a piece of nitrocellulose membrane (0.3 cm×0.5 cm, A100, 12 µm, Schleicher and Schuell, Dassel, Germany) which was kept down by tape. As sucking membrane (9 in FIG. 1), a cellulose filter (0.5 cm×2 cm, GB 004, Schleicher and Schuell, Dassel, Germany) was mounted by tape so that it overlapped the free end of the strip derived from the detection membrane.

Carbon Particle Conjugate (R*)

Carbon Suspension (Stock Solution)

2 g of carbon particles (sp 4, Degussa, Germany) were suspended in 100 ml of 5 mM borate buffer, pH 8.4, and sonicated with the same apparatus as in Example 1 in an ice-bath for 5 minutes at 100% amplitude and 5+5 seconds pulse.

Carbon-particle Conjugate

100 µg/ml of anti-transferrin monoclonal antibody and carbon suspension (250 µg/ml) were mixed for 2 hours. BSA was added to 1% and the particles were mixed for another 30 minutes and then washed by means of centrifugation in 0.1 M borate buffer, pH 8.5 (containing 1% BSA and 0.05% NaN$_3$) and diluted to 1.9 mg carbon/ml with wash buffer. The ready carbon particle conjugate was stored at +4° C. in wash buffer.

Sample Materials

Tetrasialo-transferrin

Tetrasialo-transferrin was isolated from an iron-saturated preparation of human transferrin (mainly tetrasialo-transferrin) by ion-exchange chromatography on Mono Q (Amersham Pharmacia Biotech AB, Uppsala, Sweden).

Asialo-transferrin

An iron-saturated preparation of transferrin (Sigma, St Louis, Mo., USA) was treated with neuramidase (Behringwerke, Marburg, Germany), whereupon asialo-transferrin was isolated by ion-exchange chromatography on Mono Q (Amersham Pharmacia Biotech AB, Uppsala, Sweden).

Isoelectric Points (pI)

These values were determined for the respective isoform preparation and for BSA by isoelectric focusing in Phast System (Amersham Pharmacia Biotech AB, Uppsala, Sweden). Asialo-form pI=5.7, tetrasialo-form pI=5.3 and bovine serum albumin pI=4.7.

Transferrin Standard

Asialo-transferrin prepared as above was diluted in 20 mM BIS-TRIS pH 6.3 containing 0.2% BSA, 0.1% Tween 20, 0.1 mM Fe$^{3+}$-citrate, 1 mM NaHCO$_3$ and 0.05% NaN$_3$ to the concentrations 0.07–16.6 µg transferrin/ml and was used as standard.

Serum Samples 11 serum samples and 6 serum controls were diluted 1/50 in 20 mM BIS-TRIS pH 6.3 containing 0.1% bovine gammaglobulin (Sigma, St Louis, U.S.A.), 0.1% Tween 20, 0.1 mM Fe$^{3+}$-citrate, 1 mM NaHCO$_3$, and 0.05% NaN$_3$. The serum samples were previously analysed with regard to CDT by means of CDTect (Pharmacia & Upjohn Diagnostics AB, Uppsala, Sweden). CDTect measures CD-transferrin.

Standard Protocol for Combined Separation and Immunochemical Determination

2 µl of sample (dilution series of transferrin and diluted serum samples, respectively) were applied at 1 cm from the edge (ASZ=3 in FIG. 1) of the free end of the membrane part with separation zone on a combination strip according to the above. A lateral liquid flow was initiated by placing a 0.6 cm×0.6 cm×0.3 cm cellulose sponge (8 in FIG. 1) soaked with 20 mM BIS-TRIS buffer, pH 6.5, containing 15 mM NaCl and 0.1% Tween 20 on the free end of the separation zone. In the separation zone (5 in FIG. 1) the analyte (CD-transferrin) and its heteroforms (other transferrins) are attracted by positive charges firmly anchored in the zone (Ligand introduced in the PEI treatment) so that a heteroform having a greater negative charge (other transferrins) is attracted more than a heteroform having a smaller negative charge (CD-transferrin), i.e. CD-transferrins migrate easier with the liquid flow than trisialo-, tetrasialo-, pentasialo- etc transferrin. During its migration through the combination strip/matrix, a certain proportion of the total amount of transferrin will therefore be able to bind to the anti-transferrin antibody (Capturer) in the detection zone (DZ=4 in FIG. 1). After 4 minutes flow, 5 µl of conjugate (R*) between carbon particles and anti-transferrin antibody (1.8 mg carbon/ml in 0.1 M borate buffer, pH 8.4, containing 30% trehalose, 1 % Tween 20, 1% BSA, 0.05% NaN$_3$) were added between the separation zone and the detection zone (in zone (6) in FIG. 1 (=AR*Z)). After another 5 minutes, the flow was stopped and the blackening in the detection zone was read with a laser scanner (Ultroscan, Amersham Pharmacia Biotech AB, Uppsala, Sweden) and the concentration was calculated by reading against measurement values for the dilution series of asialo-transferrin. The higher the level of CD-transferrin is in the sample, the stronger is the blackening signal.

TABLE 2

Results

| Sample | CDTect U/L | Invention arbitrary units/L |
|---|---|---|
| 1 | 5 | 0.09 |
| 2 | 11 | 0.24 |
| 3 | 13 | 0.22 |
| 4 | 17 | 0.30 |
| 5 | 18 | 0.49 |
| 6 | 22 | 0.44 |
| 7 | 22 | 0.57 |
| 8 | 26 | 0.55 |
| 9 | 26 | 0.64 |
| 10 | 38 | 0.87 |
| 11 | 40 | 1.24 |
| 12 | 40 | 1.51 |
| 13 | 58 | 1.71 |
| 14 | 78 | 1.60 |

TABLE 2-continued

Results

| Sample | CDTect U/L | Invention arbitrary units/L |
|---|---|---|
| 15 | 86 | 2.18 |
| 16 | 90 | 2.85 |
| 17 | 110 | 3.36 |

The measurement values obtained with the method of the invention showed very good conformity with those obtained with CDTect (correlation coefficient 0.971). The invention is considerably faster and simpler to perform than CDTect.

Example 3
Test Strip with *Sambucus Nigra* Lectin in the Separation Zone
Separation Membrane A sheet (4 cm×12 cm) of cellulose (cellulose filter 54, Whatman International Ltd, England) was activated with cyano-diethyl-aminopyridine (CDAP) (Kohn and Wilchek, Appl. Biochem. Biotechnol. 9 (1984) 285–304). The activated sheet was placed in a solution of 0.1 mg/ml of *Sambucus Nigra* lectin (binds sialic acid which is in the terminal position of a carbon chain; Vector Laboratories Inc., Burlingame, Calif., U.S.A.) in 0.1 M NaHCO$_3$, pH 8.4. The solution was shaken for 2 hours, and the sheet was then placed in a) 0.1 M NaHCO$_3$, b) 0.5 M NaCl, c) distilled water, d) 0.1 M acetate buffer, pH 4.5, e) 0.1 M NaHCO$_3$, pH 8.4, f) 0.5 M NaCl, g) distilled water, h) 0.1 M acetate buffer, pH 4.5, i) 5 mM BIS-TRIS, pH 6.4, containing 0.1% Tween 20. Between the different baths, excess liquid was sucked off by means of kitchen roll paper. After the wash procedure, the sheet was air-dried and stored in a plastic bag at +4° C.

Before the sheet was used, the sheet was mounted to self-adhering plastic (75 μm self-adhering polyester film; Gelman Science Inc, Ann Arbor, Mich., U.S.A.).
Membranes with Detection Zone and Combination Strip These membranes can be produced in analogy with Example 2. See also FIG. 1. The ligand in SZ is now lectin.
Carbon-particle Conjugate (R*) and $^{125}$I-labelled Proteins.
See Example 2.
Control of Separation Membrane by Means of $^{125}$I-labelled Proteins Tetrasialo- and asialo-transferrin and bovine albumin were labelled with $^{125}$I (Chloramine T, labelling degree 0.08–0.13). The labelled proteins were diluted in 10 mM BIS-TRIS pH 6.4 containing 0.1% Tween 20, 0.04 mM Fe$^{3+}$-citrate and 0.05% NaN$_3$ to about 0.3 μg/ml. Additionally, 0.4 mg BSA/ml was added.

A (0.5 cm×4 cm) strip of the separation membrane and a piece of a sucking membrane of cellulose (0.5 cm×2 cm, GB004, Schleicher and Schuell, Dassel, Germany) were joined by tape on the underside so that their ends overlapped somewhat. 1 μl of the solutions of the $^{125}$I-labelled proteins were applied at 1 cm from the free end of a respective separation membrane. The lateral flow was initiated by placing a cellulose sponge (0.6 cm×0.6 cm×0.3 cm) on the free end of the separation membrane. The sponge was soaked with 20 mM TRIS-HCL buffer, pH 7.5, containing 0.5 M NaCl, 1 mM CaCl$_2$ with 0.1% Tween 20. The flow was interrupted by removing the cellulose sponge after 2, 4, 6 and 10 minutes, respectively, and the membranes were cut 2 and 3 cm from the free end of the separation membrane. The radioactive membrane pieces were measured in a gamma counter and the proportion of added $^{125}$I-protein that had passed 2 and 3 cm was calculated. The values for migration of 1 cm or more is shown in Table 4.

TABLE 4

% of totally added $^{125}$I-protein that had migrated more than 1 cm in the separation membrane:

| | % of total | | |
|---|---|---|---|
| PI Migration time min | 5.7 Asialo-transferrin | 5.3 Tetrasialo-transferrin | 4.7 BSA |
| 2 min | 54 | 10 | 86 |
| 4 min | 74 | 10 | 87 |
| 6 min | 78 | 11 | 91 |
| 10 min | 91 | 11 | 92 |

Conclusion

It appears from the results that tetrasialo-transferrin is heavily retarded in the separation membrane by the *Sambucus Nigra* lectin, while asialo-transferrin and BSA are not retarded to the same extent. The results indicate that a separation membrane with *Sambucus Nigra* lectin may be combined with a detection membrane in analogy with Example 2 and be used for quantifying CD-transferrin in samples containing transferrin with a greater content of sialic acid than CD-transferrin.

What is claimed is:

1. A method for determining an analyte in a sample comprising the steps of:
    i. applying the sample to an application zone for sample (ASZ) on a flow matrix in which transport of constituents present in the sample may take place in a transport flow, the flow matrix further comprising:
        a) an application zone (AR*Z) for an analytically detectable binding reactant (R*),
        b) a detection zone (DZ) which is located downstream of the ASZ and comprises another binding reactant (Capturer) firmly anchored to the matrix, so that a signal complex containing the Capturer and the analyte and/or R* is formed, and
    ii. detecting the signal complex in the detection zone DZ, the measured signal being used for determining the analyte,
    wherein the flow matrix comprises at least one separation zone (SZ) between the ASZ and the DZ, the SZ comprising an immobilized chemical structure which binds to at least one component present in the sample, without using the SZ as a mechanical obstacle, so that said component(s) substantially does (do) not disturb the detection of the analyte in the DZ.

2. The method according to claim 1, wherein said component is a heteroform of the analyte, capable of binding to either the Capturer and/or to the R*.

3. The method according to claim 1 or 2, wherein the transport flow is driven by capillary forces.

4. The method according to claim 3, wherein at least the DZ and adjacent portions of the flow matrix are a membrane, and the transport flow at least into, inside, and out of the DZ is lateral.

5. The method according to any one of claims 1–2, wherein said chemical structure is a Ligand which is charged and attracts said component(s).

6. The method according to any one of claims 1–2, wherein said chemical structure is a Ligand which has biospecific affinity directed towards said component(s).

7. The method according to any one of claims 1–2, wherein said chemical structure is a Ligand which has immunochemical affinity against said component(s).

8. The method according to claim 7, wherein said ligand is selected from the group consisting of an antibody, an antigen, and a hapten.

9. The method according to any one of claims 1–2, wherein said component(s) is not the analyte and that a binding capability of the chemical structure is to a binding site on said component(s), and that this binding site is not available to the same degree on the analyte.

10. The method according to any one of claims 1–2, wherein said component is not the analyte and the Capturer has binding capability to a binding site on said component(s).

11. The method according to any one of claim 1–2 or 10, wherein said component is not the analyte and R* has binding capability to a binding site on said component(s).

12. The method according to any one of claims 1–2, wherein the analyte and said component(s) are heteroforms comprising differing carbohydrate structure.

13. A test kit for determining an analyte in a sample comprising:
A. a flow matrix for transport flow comprising:
  a) an application zone for sample (ASZ), wherein said sample comprises the analyte and disturbing component(s),
  b) a detection zone (DZ) comprising a binding reactant (Capturer) directed towards the analyte or towards an analyte-related reactant,
B. optionally an analytically detectable binding reactant (R*) having biospecific affinity to either the analyte or to the Capturer,
wherein the flow matrix comprises a separation zone (SZ) between the ASZ and the DZ, comprising chemical structure having binding capability for at least one disturbing component(s), wherein the SZ retards substantially all of said component(s).

14. The test kit according to claim 13, wherein at least the DZ and adjacent portions of the matrix are a membrane and the direction of the transport flow at least into, inside, and out of the DZ is lateral.

15. The test kit according to any one of claims 13–14, wherein the flow matrix comprises transport channels having capillary dimensions of such a form and surface character that aqueous media can be transported by capillary forces.

16. The test kit according to any one of claims 13–14, wherein the chemical structure is a Ligand which has binding capability to said component(s), wherein said component(s) are heteroforms of the analyte with regard to binding capability to the Capturer and/or to the R*.

17. The test kit according to any one of claims 13–14, wherein the chemical structure is a Ligand comprising at least one or more positive and/or negative charges.

18. The test kit according to any one of claims 13–14, wherein the chemical structure is a Ligand comprising a biospecific affinity reactant.

19. The test kit according to claim 18, wherein the Capturer is selected from the group consisting of an antibody an antigen, and a hapten.

20. The test kit according to any one of claims 13–14, wherein the Capturer is a biospecific affinity reactant.

21. The test kit according to any one of claims 13–14, wherein the kit comprises the R*, and the flow matrix comprises an application zone (AR*Z) for said analytically detectable reactant, which is located upstream and/or downstream of SZ but always upstream of DZ.

22. The test kit according to claim 21, wherein said R* is pre-deposited in said AR*Z.

23. The test kit according to claim 21, wherein said AR*Z for said R* is located upstream of, downstream of, or coincides with the ASZ.

24. The test kit according to claim 23, wherein said R* is pre-deposited in said AR*Z.

* * * * *

UNITED STATES PATENT AND TRADEMARK OFFICE
CERTIFICATE OF CORRECTION

PATENT NO. : 6,737,278 B1
DATED : May 18, 2004
INVENTOR(S) : Jan Carlsson et al.

Page 1 of 1

It is certified that error appears in the above-identified patent and that said Letters Patent is hereby corrected as shown below:

Column 21,
Line 35, before "chemical structure", insert -- an immobilized --.
Line 38, change "component(s)." to -- component(s) without using the SZ as a mechanical obstacle. --.

Signed and Sealed this

Second Day of November, 2004

JON W. DUDAS
*Director of the United States Patent and Trademark Office*